United States Patent [19]

Toyoshima et al.

[11] 4,336,251
[45] Jun. 22, 1982

[54] MEDICAMENTS CONTAINING AN ORGANOSILICON COMPOUND

[75] Inventors: Shigeshi Toyoshima, Funabashi; Ryuichi Sato, Urawa; Koichi Ito, Tokyo; Toshio Shinohara, Annaka; Yasushi Yamamoto, Takasaki; Shoji Ichinohe, Annaka, all of Japan

[73] Assignee: Shin-Etsu Chemical Co., Ltd., Tokyo, Japan

[21] Appl. No.: 178,359

[22] Filed: Aug. 15, 1980

Related U.S. Application Data

[63] Continuation of Ser. No. 64,805, Aug. 8, 1979, abandoned.

[30] Foreign Application Priority Data

Aug. 15, 1978 [JP] Japan .................................. 53-99196

[51] Int. Cl.$^3$ ........................................... A61K 31/695
[52] U.S. Cl. .................................................... 424/184
[58] Field of Search .......................................... 424/184

[56] References Cited

U.S. PATENT DOCUMENTS 2,589,445  3/1952  Sommer ............................... 424/184

Primary Examiner—Jerome D. Goldberg
Attorney, Agent, or Firm—Toren, McGeady and Stanger

[57] ABSTRACT

A novel medicament which is effective as an antihypertensive agent is proposed which contains, as its effective ingredient, an organosilicon compound represented by the general formula $$R_3Si(CH_2)_nCOOH,$$

where R denotes an alkyl group having from 1 to 6 carbon atoms and n is an integer from 1 to 5 inclusive, or a therapeutically acceptable salt thereof such as a salt with an alkali metal, e.g. sodium or potassium. The effectiveness of the compound, for example, 3-trimethylsilyl butyric acid as well as the sodium and potassium salts thereof is established by the animal test undertaken with hypertensive rats.

7 Claims, 3 Drawing Figures

MEDICAMENTS CONTAINING AN ORGANOSILICON COMPOUND

BACKGROUND OF THE INVENTION

The present invention relates to a medicament containing an organosilicon compound as its main therapeutically effective ingredient or, more particularly, to a medicament which is effective as an antihypertensive agent containing an organosilicon compound as the therapeutically effective ingredient.

In recent years, efforts have been directed to establish a novel medicament containing an organosilicon compound as the therapeutically effective ingredient utilizing the unique properties thereof hitherto not expected in any ordinary organic compounds. In particular, it is known by the inventors that several organosilicon compounds exhibit an antihypertensive effect, among which those organosilicon compounds expressed by the following chemical structural formulas

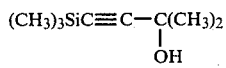

or

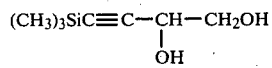

are the most highly effective ones. These organosilicon compounds are, however, not formulated practically due to the undesirable side reactions with their relatively strong toxicity. Therefore, it is an important problem in the recent pharmacological research works to establish a novel antihypertensive agent containing an organosilicon compound as its therapeutically effective ingredient.

SUMMARY OF THE INVENTION

It is an object of the present invention to provide a novel medicament as an antihypertensive agent containing an organosilicon compound as its therapeutically effective ingredient with very low toxicity.

Thus, the medicament of the present invention comprises as its therapeutically effective ingredient an organosilicon compound represented by the general formula $$R_3Si(CH_2)_nCOOH, \qquad (I)$$

where R denotes an alkyl group having from 1 to 6 carbon atoms and n is a positive integer from 1 to 5 inclusive, or a therapeutically acceptable salt thereof.

DETAILED DESCRIPTION OF THE PREFERRED EMBODIMENTS

Figure 1:
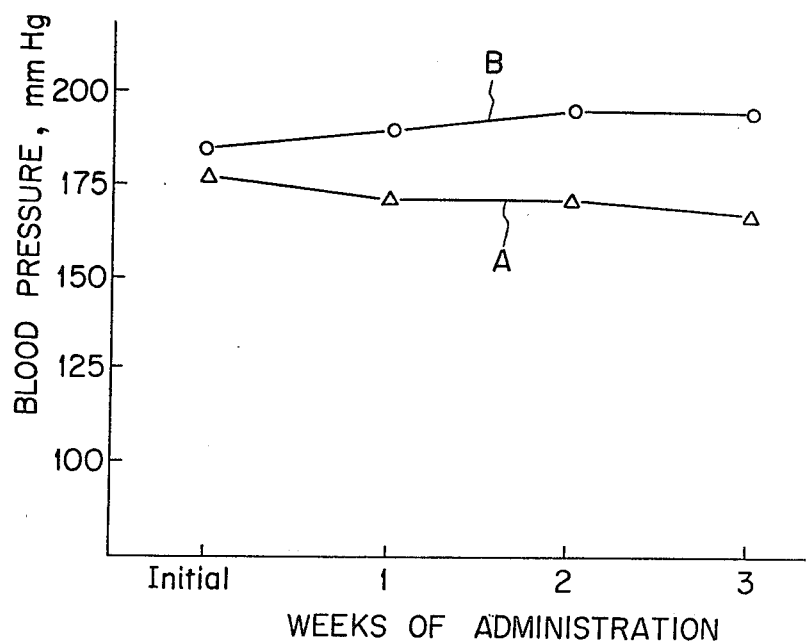
FIG. 1 shows the lowering of blood pressure in hypertensive rats by the administration of 3-trimethylsilyl butyric acid.
Curve A: test group; Curve B: control group

The present invention, which has been established as a result of the extensive investigations undertaken by the inventors, provides a novel medicament therapeutically effective both as an antihypertensive agent and the effective ingredient thereof is an $\omega$-trialkylsilyl-substituted carboxylic acid represented by the general formula (I) above given or a therapeutically acceptable salt thereof.

In the general formula (I), R denotes an alkyl group having from 1 to 6 carbon atoms, i.e. methyl, ethyl, propyl, butyl, pentyl or hexyl groups, among which methyl and ethyl groups are preferred by the reason of easiness in the synthetic preparartion although the therapeutic effectiveness of the compounds having higher alkyl groups as R is much the same as in the compounds with methyl or ethyl groups. It is of course that three of the R groups bonded to the same silicon atom can be different from each other.

Further, n in the general formula (I) is a positive integer from 1 to 5 inclusive so that the organosilicon compounds in conformity with the formula include $\omega$-trialkyl-silyl-substituted acetic, propionic, butyric, valeric and hexoic acids, among which the butyric acid derivatives are the most preferred also by the reason of easiness in the synthetic preparation.

Several of the examples of the $\omega$-trialkylsilyl-substituted carbosylic acids of the general formula (I) are as follows.

| | |
|---|---|
| 3-trimethylsilyl butyric acid | $(CH_3)_3Si(CH_2)_3COOH$ |
| trimethylsilyl acetic acid | $(CH_3)_3SiCH_2COOH$ |
| 3-triethylsilyl butyric acid | $(C_2H_5)_3Si(CH_2)_3COOH$ |
| 3-tributylsilyl butyric acid | $(C_4H_9)_3Si(CH_2)_3COOH$ |
| 2-trimethylsilyl propionic acid | $(CH_3)_3Si(CH_2)_2COOH$ |

Furthermore, several kinds of salts of the above given acids are also effective and therapeutically acceptable. The countercations in these salts are not limitative insofar as no adverse effects are induced by the presence of the cations. These salts have generally larger solubility in water than the free acid and suitable for administration as an aqueous solution while the free acids are used sometimes as dissolved in olive oil or the like. In this respect, salts of alkali metals, e.g. sodium, potassium and lithium, are recommended although the other kinds of metal salts such as calcium salts are also employed.

The acute toxicity by oral administration of the above mentioned organosilicon compounds in the acid form as well as in the salt form is as low as to give a value of $LD_{50}$ of about 3,000 to 3,100 mg/kg as determined with rats as the test animals. Despite the above given very low toxicity, these compounds are effective in reliably lowering the blood pressure when orally administrated to hypertensive rats.

The $\omega$-trialkylsilyl-substituted carboxylic acid of the general formula (I) can be synthesized by the Grignard's reaction starting with the corresponding $\omega$-halogenoalkyl trialkylsilane which is reacted with metallic magnesium followed by the reaction with carbon dioxide and subsequent hydrolysis in accordance with the following reaction equations (see, for example, L. H. Sommer et al. Journal of the American Chemical Society, vol. 71, 1949, page 1509), in which X is a halogen atom such as a chlorine atom, the other symbols having the same meaning as defined above.

$$R_3Si(CH_2)_nX + Mg \rightarrow R_3Si(CH_2)_nMgX$$

$$R_3Si(CH_2)_nMgX + CO_2 \rightarrow R_3Si(CH_2)_nCOOMgX$$

$$R_3Si(CH_2)_nCOOMgX + H_2O \rightarrow R_3Si(CH_2)_nCOOH + Mg(OH)X$$

The corresponding salts of the above obtained silicon-containing carboxylic acid with a metal such as an alkali metal or an alkaline earth metal is prepared by merely neutralizing the above acid with respective hydroxide of the metal such as sodium hydroxide.

Following are the illustration of the synthetic preparation of the ω-trialkylsilyl-substituted carboxylic acid of the general formula (I) and a salt thereof in further detail taking 3-trimethylsilyl butyric acid and sodium salt thereof as the typical examples.

Preparation of 3-trimethylsilyl butyric acid and sodium 3-trimethylsilyl butyrate:

Reaction was carried out with 196 g (1.3 moles) of 3-chloropropyl trimethylsilane and 34 g (1.4 moles) of metallic magnesium in 500 ml of diethyl ether to form 3-trimethylsilylpropyl magnesium chloride, and solid carbon dioxide, i.e. dry ice, was added to the reaction mixture while the temperature of the reaction mixture was kept not to exceed 5° C. by cooling from outside in an ice bath.

After completion of addition of dry ice followed by washing with water to effect the hydrolysis and to remove the magnesium salt, the reaction mixture was subjected to extraction with diethyl ether and distillation of the ether extract under reduced pressure gave 187 g of a colorless, transparent liquid product which was identified to be 3-trimethylsilyl butyric acid by the boiling point of 97° C./4.5 mmHg and the refractive index $n_D^{25}$ of 1.4339 in good coincidence with the values given in literatures. The above yield of the product was about 90% of the theoretical value.

Into an aqueous solution of 6.0 g (0.15 mole) of sodium hydroxide in 100 ml of water was added 25.6 g (0.16 mole) of the above obtained 3-trimethylsilyl butyric acid with agitation and the unreacted free acid was removed by extraction with diethyl ether. The aqueous solution was subjected to evaporation of water under reduced pressure to dryness to give 27.3 g of a white powdery product of sodium 3-trimethylsilyl butyrate.

In the following, examples are given to illustrate the effectiveness of the thus prepared 3-trimethylsilyl butyric acid or the alkali metal salts thereof as an antihypertensive agent with test animals.

EXAMPLE 1

Effectiveness of 3-trimethylsilyl butyric acid as an antihypertensive agent was examined with hypertensive rats as the test animals. Hypertensive rat is known to exhbit spontaneous hypertension and useful as a model animal for the condition of illness in hypertension of human.

3-Trimethylsilyl butyric acid was orally administered to six of the hypertensive rats with body weights of each 200 to 220 g in a uniform dose of 100 mg/kg/day as dissolved in olive oil in a concentration of 5% by weight to measure the blood pressure every week. The results were as shown by Curve A in FIG. 1 obtained by plotting the average value for the six rats. Control test was undertaken in parallel by administrating same amounts of olive oil alone to the other group of six hypertensive rats to give the results shown by Curve B in the same figure.

EXAMPLE 2

The same test procedure as in the preceding example was repeated with the hypertensive rats as the test animals except that the olive oil solution of 3-trimethylsilyl butyric acid in Example 1 was replaced with an aqueous solution of sodium 3-trimethylsilyl butyrate in the same concentration.

Figure 2:
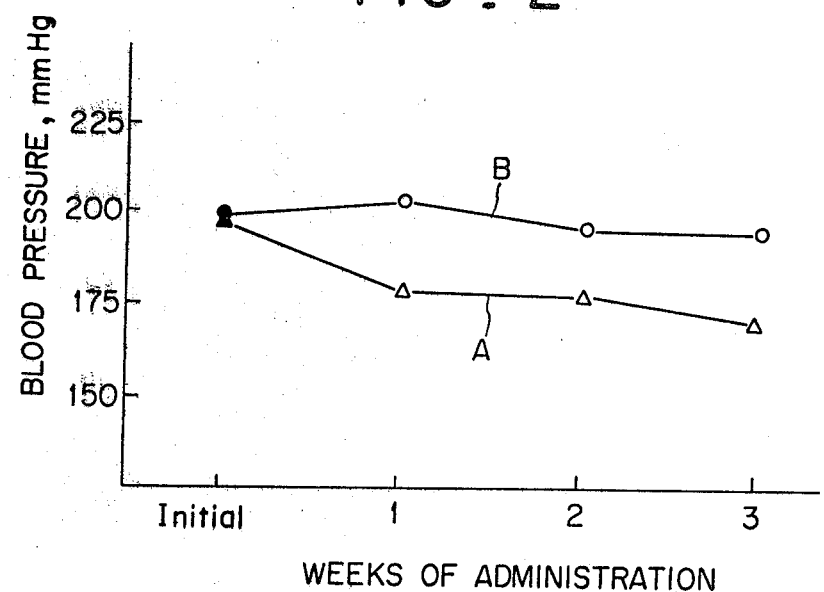
FIG. 2 shows the lowering of blood pressure in hypertensive rats by the administration of sodium 3-trimethylsilyl butyrate.
Curve A: test group; Curve B: control group

The results of the test and the results of the control test carried out by administrating same amounts of water alone are shown by Curves A and B in FIG. 2, respectively.

EXAMPLE 3

Figure 3:
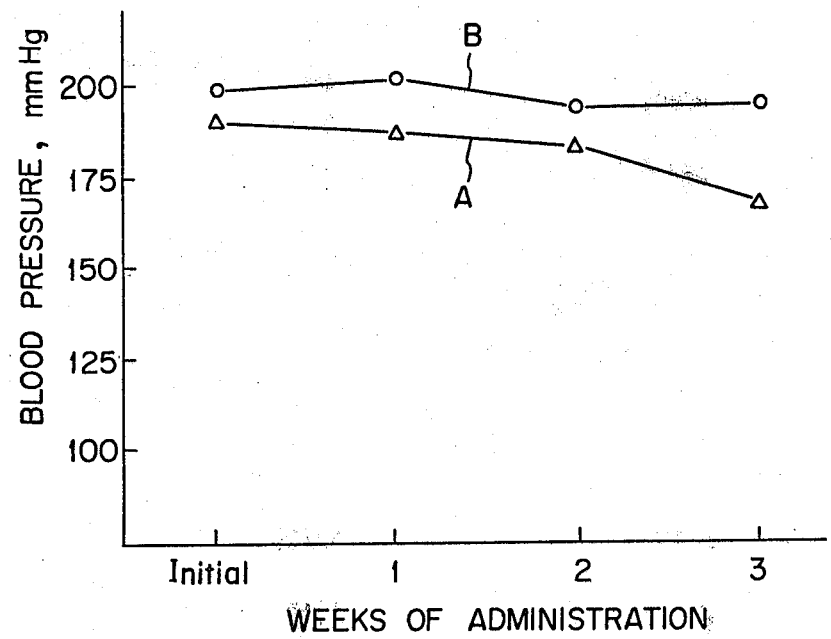
FIG. 3 shows the lowering of blood pressure in hypertensive rats by the administration of potassium 3-trimethylsilyl butyrate.
Curve A: test group; Curve B: control group

Potassium 3-trimethylsilyl butyrate was orally administrated to the hypertensive rats in a dose of 100 mg/kg/day as dissolved in drinking water in a concentration of 0.1% by weight allowing the test animals to freely drink it up to a predetermined volume. FIG. 3 illustrates the lowering of blood pressure in the test animals (Curve A) together with the results of the control test (Curve B) carried out in parallel by administrating the amounts of the drinking water alone.

What is claimed is:

1. A method for treating hypertension in human patients comprising administering to the patient a medicament composed of a carrier and an anti-hypertensive effective amount of an organosilicon compound represented by the formula $$R_3Si(CH_2)_nCOOH,$$

where
R denotes an alkyl group having from 1 to 6 carbon atoms, and
n is an integer from 1 to 5 inclusive,
or a therapeutically acceptable salt thereof.

2. The method of claim 1 wherein the alkyl group denoted by the symbol R is a methyl group.

3. The method of claim 1 wherein the alkyl group denoted by the symbol R is an ethyl group.

4. The method of claim 1 wherein n is 3.

5. The method of claim 1 wherein the therapeutically acceptable salt is an alkali metal salt.

6. The method of claim 5 wherein the alkali metal is sodium.

7. The method of claim 5 wherein the alkali metal is potassium.

* * * * *